United States Patent
Uda et al.

(10) Patent No.: US 7,525,651 B2
(45) Date of Patent: *Apr. 28, 2009

(54) INSPECTION APPARATUS AND INSPECTION METHOD FOR PATTERN PROFILE, AND EXPOSURE APPARATUS

(75) Inventors: Mitsuru Uda, Shiga-ken (JP); Kazunari Terakawa, Shiga-ken (JP); Akira Susuki, Shiga-ken (JP); Chiaki Oishi, Shiga-ken (JP); Yasuharu Yamada, Shiga-ken (JP); Teruhiko Havano, Shiga-ken (JP)

(73) Assignee: International Business Machines Corporation, Armonk, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/924,126

(22) Filed: Oct. 25, 2007

(65) Prior Publication Data
US 2008/0192257 A1  Aug. 14, 2008

Related U.S. Application Data

(63) Continuation of application No. 10/497,053, filed on Feb. 10, 2005, now Pat. No. 7,310,141.

(30) Foreign Application Priority Data
Nov. 30, 2001 (JP) ............................. 2001-367400

(51) Int. Cl.
*G01N 21/00* (2006.01)

(52) U.S. Cl. ................................ 356/237.5; 356/237.2
(58) Field of Classification Search ...................... None
See application file for complete search history.

(56) References Cited

FOREIGN PATENT DOCUMENTS

| JP | 63-305512 | 12/1988 |
|----|-----------|---------|
| JP | 10325805 | 12/1998 |
| JP | 11051874 | 2/1999 |

*Primary Examiner*—Michael P Stafira
(74) *Attorney, Agent, or Firm*—Scully, Scott, Murphy & Presser, P.C.; Robert M. Trepp, Esq

(57) ABSTRACT

Disclosed is a pattern inspection apparatus which easily and highly accurately detects a profile error (deviation) of at least one pattern having a cross section with projections and recesses. The inspection apparatus for the pattern 32 is for detecting the profile error of the pattern having a cross section with a projection and a recess. This inspection apparatus includes a plate 30 on which a pattern is mounted, light sources 40, 42 and 44 which can change angles of illuminating light emitted onto the pattern, within a range of 15 to 75 degrees with reference to the top surface of the pattern, and photodetectors 52 and 54 which can receive reflected light from the pattern at an angle within a range of 15 to 75 degrees with reference to the top surface of the pattern. The inspection apparatus is characterized by that the profile error of the pattern is detected based on an amount of the reflected light from an edge between the top surface and the side surface of each of the patterns.

15 Claims, 8 Drawing Sheets

θ: Reflection Angle
θin: Reflection Angle
θo: Resist Edge Angle

INSPECTION APPARATUS AND INSPECTION METHOD FOR PATTERN PROFILE, AND EXPOSURE APPARATUS

RELATED APPLICATIONS

This application is a continuation of U.S. patent application Ser. No. 10/497,053, filed Feb. 10, 2005.

TECHNICAL FIELD

The present invention generally relates to a pattern inspection apparatus which detects a profile error (deviation) of a pattern having a cross section with projections and recesses, and more particularly to an inspection apparatus and an inspection method which determine presence and absence of defective deformation of a photoresist pattern formed on a substrate such as a wafer.

BACKGROUND ART

In a manufacturing process of semiconductor devices, a photoresist pattern hereinafter, simply referred to as a resist pattern) is formed on a wafer as a mask for forming a circuit pattern. The resist pattern is formed in a manner that a mask pattern is exposed onto a resist applied on the wafer, using a stepper or a scanning exposure equipment, and then an exposed portion or an unexposed portion is removed (developed). When performing fine patterning of various patterns of semiconductor devices, it is particularly important to fabricate the resist pattern with good accuracy to conform to its design dimensions as much as possible.

The resist pattern may not be property formed as designed because of a defocus (out of focus) or the like during exposure. Specifically the resist pattern is formed, deviating from the design dimensions. When the wafer is mounted on a mounting stage, adsorbed to maintain a surface of the wafer flat and then exposed, this defocus occurs when the surface of the wafer is not flat due to a foreign matter such as dirt and dust between the back surface of the wafer and the surface of a stage, or when the height of the resist surface is uneven for various reasons such as nonuniform application of the resist.

Conventionally, defective formation (profile error) of the resist pattern due to a defocus has been inspected utilizing diffracted light which is generated when the resist pattern is illuminated with light as diffraction grating. For example, in Japanese Patent Laid-Open Publication No. 2001-141657, presence or absence of a defocused portion is detected by capturing a color difference which is considered a diffraction angle difference of diffracted light which is generated from the defocused portion and a normal portion of the resist pattern.

As miniaturization of semiconductor devices has advanced, a pitch of the pattern formed on the wafer has become too small to generate the diffracted light using visible light. For example, in order to generate diffracted light from a fine wafer with a pitch of about 0.1 micrometers (100 nm), light in an ultraviolet region with a shorter wavelength (400 nm or shorter) than that of the visible light must be used as a light source, as described in, for example, Japanese Patent Laid-Open Publication No. 2000-338049. However, when ultraviolet light is used, the resist pattern is exposed. Further, since ultraviolet light is invisible to humans, setting of the optical system or measurement of the diffracted light requires enormous effort and time. Furthermore, an ultraviolet sensor used as a photodetector is expensive, and it is sometimes difficult to even procure an ultraviolet sensor for a large area.

Moreover, to utilize the diffracted light means that the diffraction angle is varied depending on a difference of patterns on the wafer. Specifically, it is required to carry out a macro observation in which the defective formation of the resist pattern due to defocus is observed from every angle and direction, and this has been a great disadvantage in reducing inspection time and automating the macro inspection.

An object of the present invention is to easily and highly accurately detect a profile error (deviation) of a pattern having a cross section with projections and recesses.

Another object of the present invention is to easily determine presence or absence of a defocus of a resist pattern.

DISCLOSURE OF THE INVENTION

In the present invention, a profile error of a pattern is detected by monitoring an amount of reflected light from an edge between top and side surfaces of the pattern having a cross section with projections and recesses. Specifically, the present invention detects a profile error of a pattern, considering that the profile error of the pattern including the edge is small when the amount of reflected light which is received by a photodetector from the edge of the pattern is large, and, on the contrary, the profile error of the pattern including the edge is large when the amount of reflected light from an edge is small.

The present invention provides a new optical system for detecting a profile error of a pattern by monitoring the amount of reflected light from an edge between top and side surfaces of a pattern having a cross section with projection and recess. In that case, the present invention has a characteristic to microscopically and highly accurately detect a profile error of a fine pattern by a simple optical system using visible light for general use, without utilizing ultraviolet light and diffracted light.

BRIEF DESCRIPTION OF THE DRAWINGS

FIG. 3(a) is a schematic view of a resist pattern inspection, and FIG. 3(b) is an enlarged view of a main part of FIG. 3(a).

BEST MODES FOR CARRYING OUT THE INVENTION

In description below, although only a resist pattern is used, an application target of the present invention is not limited thereto, and the present invention can be applied to all patterns, each having at least a plurality of continuous projections and recesses (thickness). For example, the present invention may be applied to a fine conductor circuit pattern on a semiconductor device, grating for a semiconductor laser, a color filter and the like.

Figure 1:
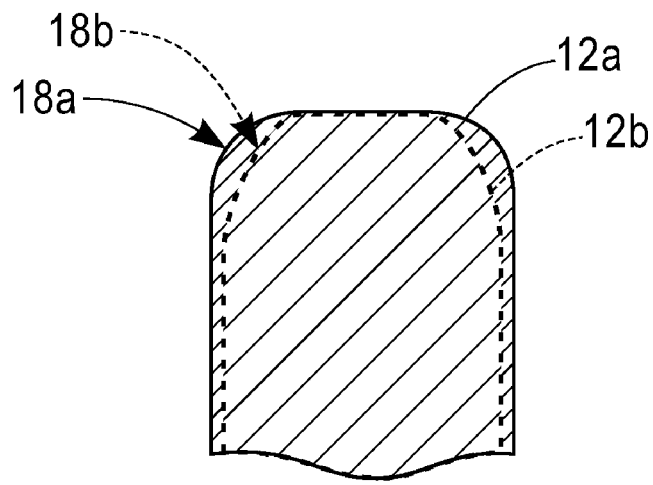
FIG. 1 is a view comparing a edge shape of a resist pattern of a defocused portion and that of a normal resist pattern.

A detection principle of the present invention is described before detailing an embodiment of the present invention. A profile error of a pattern appears conspicuously at an edge between the top and side surfaces of the pattern (hereinafter, simply referred to as an edge). With the profile error (deviation), the shape of the edge deviates from the original shape that the edge should have. For example, as shown in FIG. 1, the edge 18b of the resist pattern 12b is curved more sharply than the edge 18a of the normal resist pattern 12a. Specifically, the edge 18b is curved inwardly. This is because a fuzzy image (mask pattern) is transferred to the resist due to the defocus during exposure.

Figure 2:
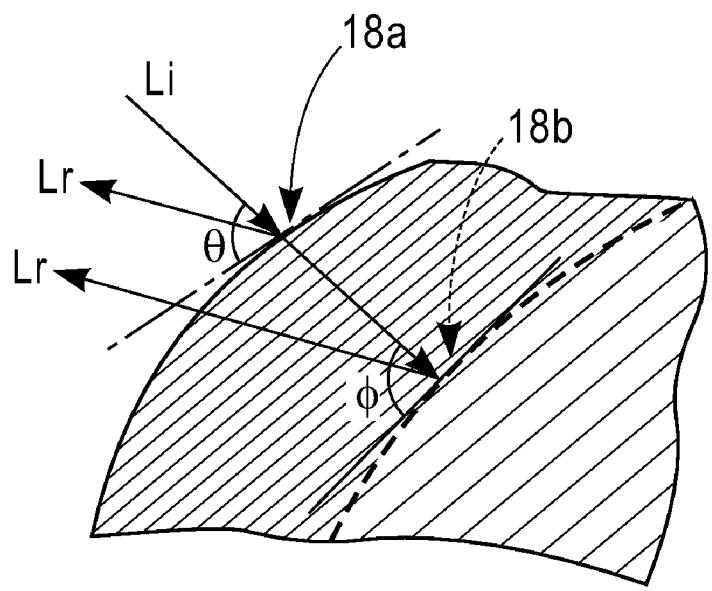
FIG. 2 is a view showing a difference in incident angles of illuminating light from the resist pattern of the defocused portion and the normal resist pattern.

Therefore, as shown in FIG. 2, the edge 18a of the normal resist pattern 12a and the edge 18b of the defocused resist pattern 12b are respectively different in incident angles θ and ❷ of illuminating light Li with reference to the edges, and thus the angles of reflected light Lr with reference to the illuminating light Li are different. Specifically, the reflection angle of the reflected light from the edge, out of incident light to the pattern, changes in accordance with an inclination degree (angle) of the edge. When the position (for example, an angle with reference to the top surface of the pattern) of the photodetector to receive the reflected light is fixed at a certain position (angle), the amount of reflected light from the edge entering into the photodetector changes in accordance with the inclination degree (angle) of the edge. Specifically, as the inclination degree (angle) of the edge becomes larger, in other words, as the defocus becomes larger, the amount of reflected light from the edge entering into the photodetector becomes smaller. As a result, the profile error of the pattern can be sensed by detecting the amount of reflected light from the edge.

By relatively comparing the amounts of reflected light from the edge for each of the edges or for each certain areas, the presence or absence and the distribution of the profile errors in the patterns arranged two dimensionally can be macroscopically obtained. In other words, even when the patterns are formed two dimensionally over a wide area, the profile errors of the patterns can be obtained as a two dimensional distribution (macroscopic) by measuring the patterns while scanning each appropriate area.

In the present invention, the detection principle thereof is fundamentally different from that of the conventional method using a diffracted light or coherent light. Specifically, in the present invention, the largest possible amount of reflected light from the edge is detected by excluding (so as not to detect) diffracted light and coherent light as much as possible. Accordingly, used in the present invention are a positioning of the optical system, a characteristic of an optical element and the like which are different from those of the conventional method. In the present invention, in order to obtain the maximum detection sensitivity, used are, for example, a positioning of the optical system, characteristics of an optical element and the like as described below, which are different from those of the conventional method.

(a) A uniform surface emitting light source is preferred as a light source.

(b) The light source is preferably located at a position where the edge portion of the resist is illuminated with light. Alternatively, the light source is located so that the uniform surface emitting light source can be observed by the photodetector.

Further, it is preferable that light be incident to the edge between the top and side surfaces of the pattern, from an almost perpendicular direction with reference thereto.

(c) It is preferable that the light source be a luminous flux with directivity of a predetermined angle (for example, about 35 degrees) or smaller.

(d) It is preferable that the light source have an oblong (stick-like) shape, for example, a size of 20 mm % 300 mm, for giving the luminous flux directivity.

(e) A CCD, for example, can be used as the photodetector, and a line sensor type CCD which is capable of detecting light with directivity is preferred to an area sensor type CCD.

The pattern inspection apparatus and inspection method of an embodiment of the present invention is described in detail hereinbelow using the drawings. In this specification, as an example, description is provided regarding a case of inspecting a resist pattern in which a silicon wafer is used as a substrate and which is formed after exposing a positive resist, which is applied onto the wafer, using a scanning exposure equipment, and thereafter removing unnecessary portions of the resist. Further, this resist pattern has a thickness of, for example, 0.6 to 0.7 micrometers (μm). Note that detection can be performed even when the resist has an even smaller thickness of, for example, 0.1 micrometers (μm) or smaller.

Figure 3A:
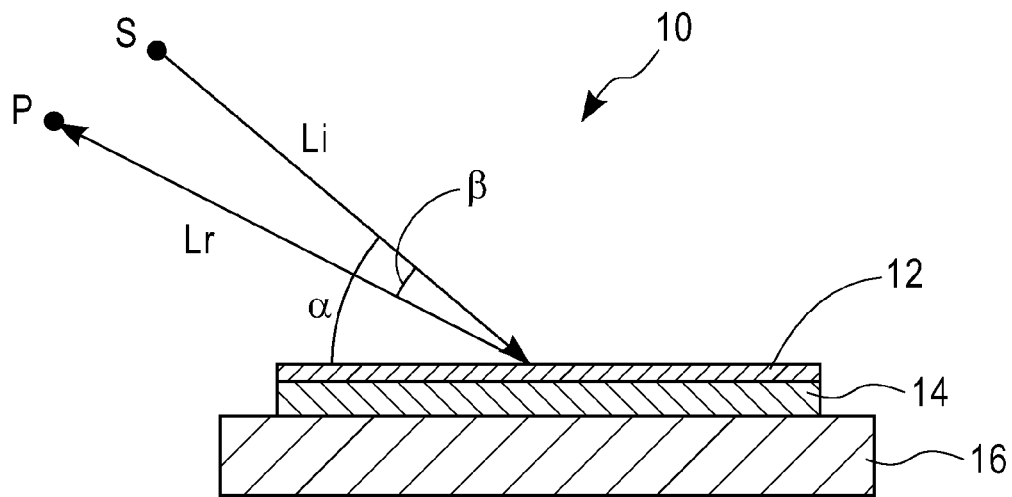
FIGS. 3(a) and 3(b) are views of a resist pattern inspection apparatus and an inspection method according to the present invention.
Figure 3B:
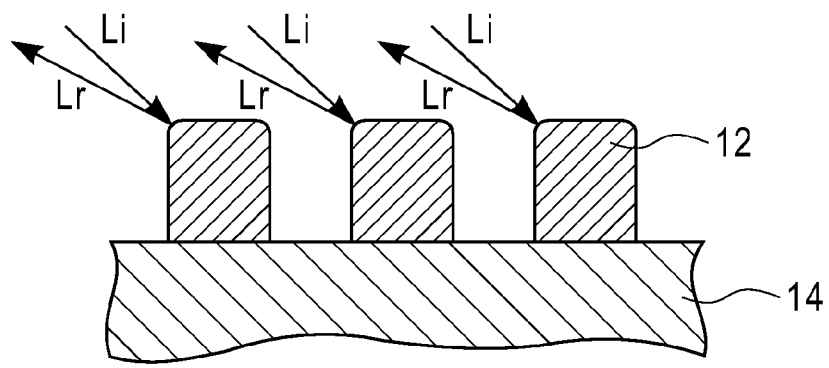

FIGS. 3(a) and 3(b) are views showing how light is illuminated and reflected in the pattern inspection apparatus of the embodiment of the present invention. The pattern inspection apparatus includes the light source S for illuminating the resist pattern 12 formed on the wafer 14 with the illuminating light Li, and a light receiving means P for receiving the reflected light Lr which is the illuminating light Li reflected by the edge of the resist pattern 12. The whole or a part of resist pattern 12 is illuminated with the illuminating light Li. The receiving means receives the reflected light Lr reflected by the edge and a smallest possible amount of reflected light from the top surface. The detection sensitivity is improved by receiving as much the reflected light Lr reflected by the edge as possible.

In FIG. 3, the stage 16, where the wafer 14 is placed, is circular and is freely rotatable in a circumferential direction about an axis, which is a line perpendicularly passing through the center point of the circle.

It is preferable that the illuminating light Li be monochromatic light for better sensitivity and visibility when the light receiving means receives the reflected light Lr. However, the illuminating light Li is not limited thereto for detection. The illuminating light Li may be light including a certain wavelength or a plurality of wavelengths similar thereto. For the light source S, a surface emitting light source is used, which is constructed as an array having a plurality of light emitting diodes (LEDs) arranged vertically and horizontally, such that the illuminating light Li illuminates the entire resist pattern 12.

In order to receive the reflected light Lr which is reflected by the edge, the wavelength of the illuminating light Li is preferably within a range of about 400 to 700 nanometers (nm) in a visible light region. In a case of using visible light, the amount of reflected light can be recognized by brightness (lightness) of the reflected light Lr. Note that, however, the illuminating light Li is not limited to visible light, and may be light with a different wavelength region such as an infrared light, as long as it does not include a wavelength which exposes the resist (ultraviolet light).

Figure 4:
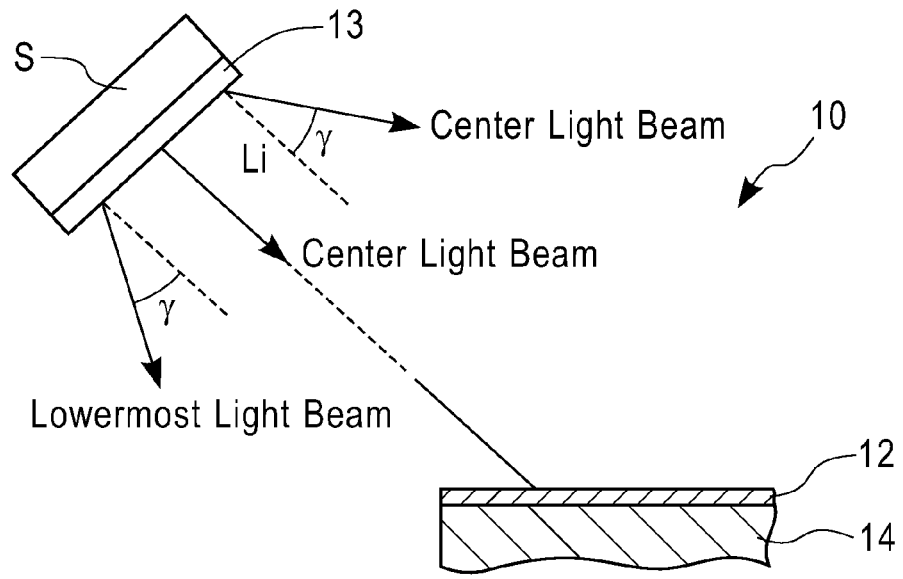
FIG. 4 is a view showing the surroundings of light including a diffusion angle γ of the illuminating light.

FIG. 4 is a view showing the surroundings of the light source of an embodiment of the present invention. In FIG. 4, a diffusion plate 13 is placed in front of the LEDs, and a diffusion angle γ (an angle of an uppermost or lowermost light beam with reference to a center light beam) of the illuminating light Li from the light source S is set to be 35 degrees or smaller. The reason why the diffusion angle γ is set to be 35 degrees or smaller is because it was learned, as a result of various tests, that this angle is optimal to improve the detection sensitivity while eliminating unnecessary light such as reflected light from areas other than the edge, diffracted light, scattered light and the like. Examples in constructions of the LED and the diffusion plate are shown below. Note that, however, the LED may be one having a different wavelength.

Examples in Constructions of LED and Diffusion Plate

LED: Dominant wavelength: 535 nm, Light intensity: 3.4 cd, Directional pattern: ±15 degrees, Number: 240, Size: 250 mm % 48 mm Diffusion plate: Transmittance: 60%

The surface emitting light source using the LEDs is preferred for uniformizing luminance of a light emitting surface to obtain a higher directivity of the illuminating light. The surface emitting light source is capable of illuminating a wide area with the illuminating light Li at once. Therefore, when the reflected light Lr is received by the light receiving means, a difference in the reflection light from the normal portion and the defocused portion can be clearly identified. Further, since the surface emitting light source can illuminate a wide area with the illuminating light Li, measurement can be carried out without moving the light source S or the substrate 14 when an inspection is conducted.

Light from the light source S is required to be emitted to the top surface of the resist pattern 12, slanting at an angle within a range of 15 to 75 degrees, more preferably 30 to 50 degrees, with reference to the top surface of the resist pattern 12. Further, it is preferable that reflected light be received by the receiving means, slanting at an angle within a range of 15 to 75 degrees with reference to the top surface of the resist pattern 12. The reasons for the above are as follows.

Figure 5:
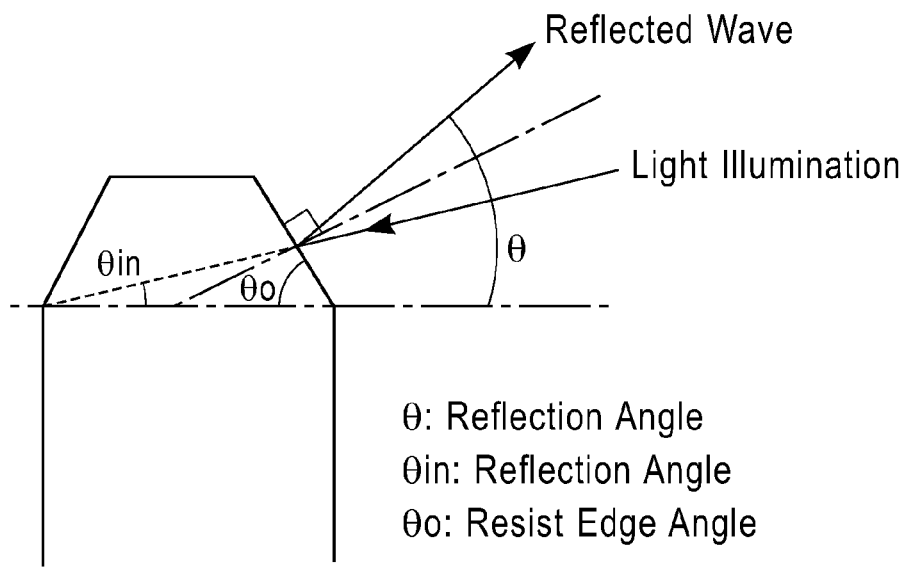
FIG. 5 is a view showing an equivalent model of the resist pattern.

From the results of the tests, it was found out that the reflected light from the resist edge generated by light illumination can be macroscopically calculated by approximating the shape of the resist using an equivalent model shown in FIG. 5. Specifically, an approximate reflection angle with reference to a light illumination (incident) angle may be obtained by the following equation:

$$\theta = 180 - \theta_{in} - 2\theta_o \quad (1)$$

wherein θ denotes the reflection angle, θin denotes the light illumination angle and θo denotes the resist edge angle.

Further, from the cross sectional shapes of the resist patterns with a plurality of line widths observed by SEM or the like, it was found out that all shapes of the resist patterns are represented by an inclination angle θo of the edge portion within a range of 30 to 70 degrees. In addition, a relationship between the reflection angle and the inclination angle of the resist edge within a range from the maximum illumination angle of 75 degrees to the minimum illumination angle of 15 degrees was obtained using equation (1). Consequently it was found out that all the reflected light from the resist edges having inclination angles within a range of 30 to 70 degrees has reflection angles between 15 and 75 degrees with respect to the light illumination angles between 15 and 75 degrees. Specifically, it was found out that the light source should cover the light illumination angles between 15 and 75 angles and the photodetector is to cover the light receiving angles between 15 and 75 degrees, when attempting to receive the reflected light from the resist edge portions of all shapes. In other words, the illuminating light Li is reflected to the opposite side of the photodetector P (FIG. 3) when the light illumination angle is 15 degrees or smaller, whereas the illuminating light Li is reflected in a direction towards the substrate 14 when the light illumination angle is 75 degrees or larger. Therefore, the reflected light Lr cannot be received by the photodetector P.

The photodetector includes, for example, a camera P using a CCD (charge coupled device) as a light receiving element. The reflected light Lr received by the CCD is converted into image data as detailed later. Image processing of the image data is her performed to detect the defocused portion. For example, with image processing, a portion where the image data suddenly changes due to the amount of the reflected light from the edge is detected as a difference in brightness (lightness), thus the normal portion and the defocused portion is distinguished. When the camera P is used, it is feasible to automate the inspection apparatus 10 as described later. Further, the human eye may be used instead of the camera P. In this case, the reflected light Lr is viewed to distinguish the normal portion and the defocused portion by the difference in the reflected light Lr.

Figure 6:
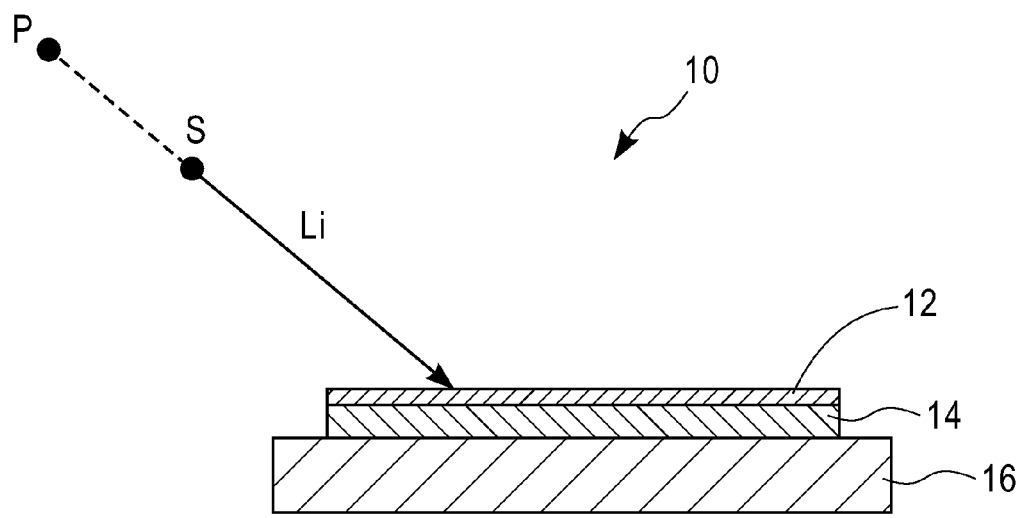
FIG. 6 is a view showing positions of a light source and an eye where the illuminating light cannot be viewed.

As mentioned earlier, the camera P is generally located at a position above the top surface of the resist pattern 12 within a range of 15 to 75 degrees with reference thereto. Further, when the reflected light Lr can be received even at the angle within a range of 15 to 75 degrees, the camera P may be located at a position within the range. However, as shown in FIG. 6, the camera P cannot identify the reflected light Lr if the light source S and the camera P are located on the same line with the illuminating light Li. Hence, the angle positions of the light source S and the camera P are required to be moved away from each other, but the light source S and the camera P are required to be located on the same side with reference to the resist pattern 12. When the light source S is located at a position at an angle within a range of 15 to 75 degrees with reference to the top surface of the resist pattern 12, an angle β formed by the illuminating light Li and the reflected light Lr is changeable within an angle range of about plus or minus 60 degrees with reference to the illuminating light Li.

It is preferable that a distance between the light source S and the resist pattern 12 be, for example, within a range of 300 to 600 mm. This is because, if the distance between the light source S and the resist pattern 12 is too long, illumination intensity on the resist pattern 12 is reduced and a contrast of the reflected light Lr is deteriorated. Thus, the defocus is overlooked. On the contrary, if the distance between the light source S and the resist pattern 12 is too short, the contrast of the reflected light Lr is deteriorated, and the illumination intensity on the resist pattern 12 becomes too high. Consequently, in the case of viewing the resist pattern 12 with a human eye, the eye gets tired easily and an illuminated area on the resist pattern 12 with the illuminating light Li becomes small.

It is also preferable that the distance between the resist pattern 12 and the camera (or the eye) P be, for example, within the range of 300 to 600 mm. This is because, if the camera P is too close to the resist pattern 12, a field of view becomes narrow, and, if the camera P is too far from the resist pattern 12, the contrast of the reflected light Lr is deteriorated.

The positions of the light source S and the camera (or the eye) P may be fixed within the above mentioned range. This is because, the angle of the reflected light Lr with reference to the illuminating light Li is constant. Therefore, the present invention can be utilized for an automatic inspection apparatus using the CCD whose demand is expected in the future.

Figure 7:
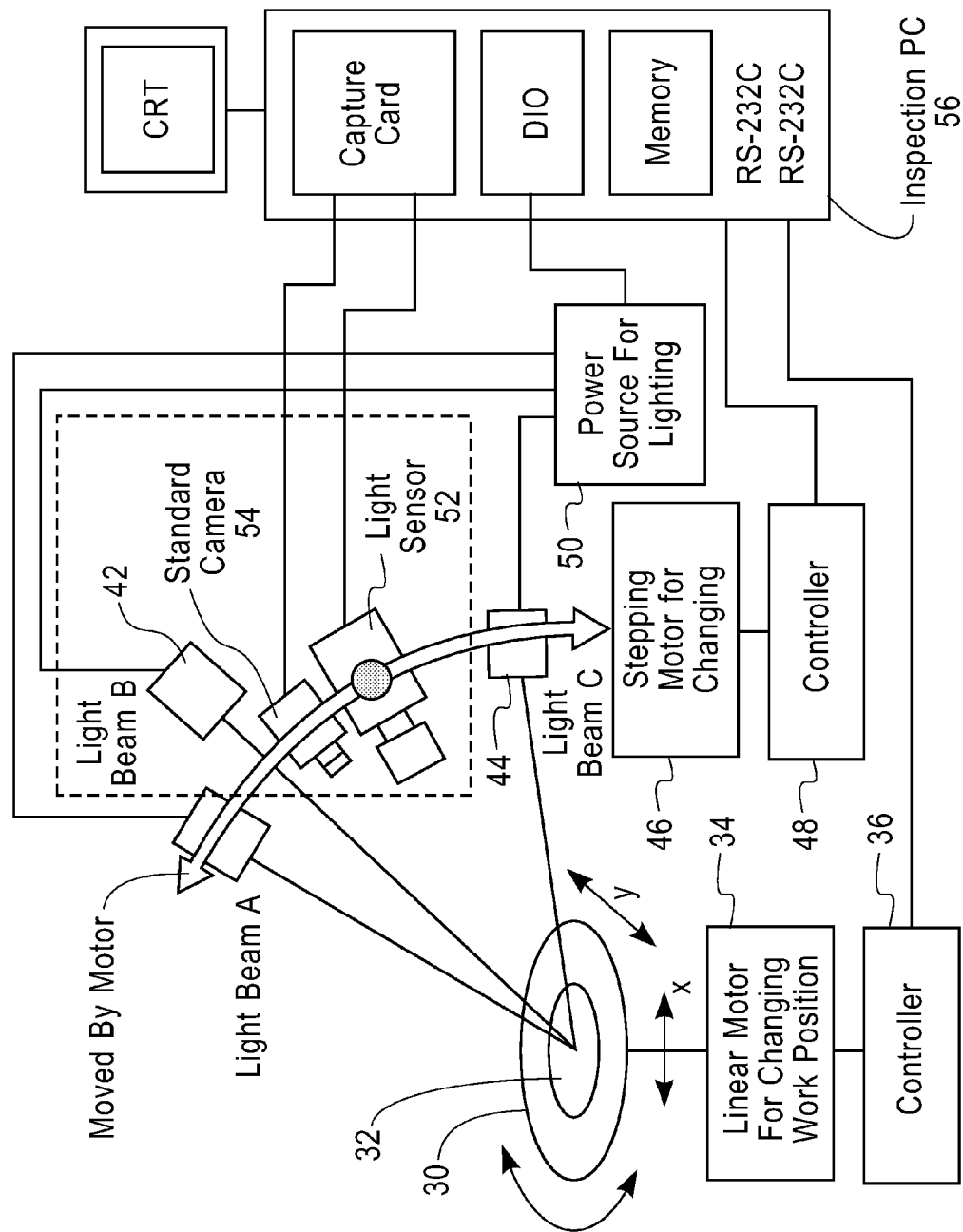
FIG. 7 is a view showing an example of an automatic inspection apparatus using a CCD of the present invention.
Figure 8:
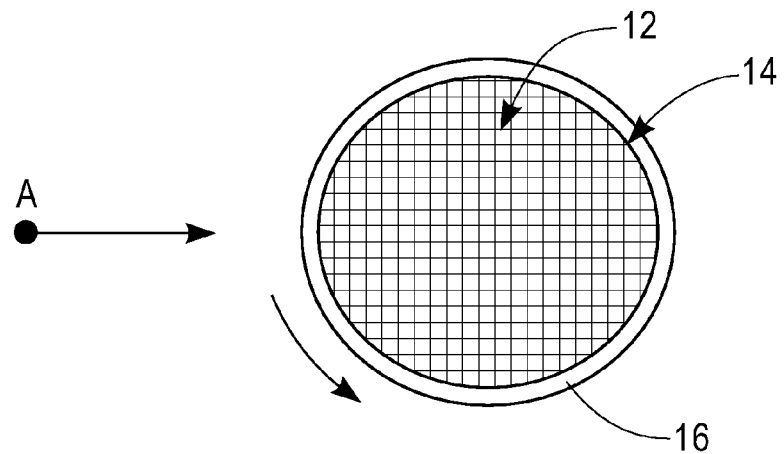
FIG. 8 is a view showing rotation of a wafer on a stage.
Figure 9:
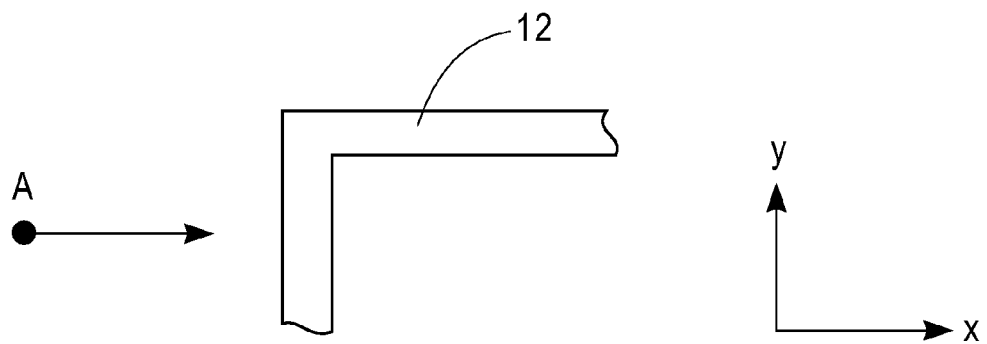
FIG. 9 is a view showing a direction in which the illuminating light is emitted onto the resist pattern.

FIG. 7 is a view showing an automatic inspection apparatus using the CCD of the embodiment of the present invention. In FIG. 7, the substrate (wafer) 32 having patterns to be measured is mounted on the circular stage (work) 30. The stage 30 is rotated or moved horizontally or vertically by a linear motor 34 controlled by a controller 36. As shown in FIG. 8, the stage 30 is rotated by 90 degrees in a circumferential direction so that the inspection can be carried out from a different direction. This is because, when the resist pattern 12 is orientated in X and Y directions and light is emitted from point A as shown in FIG. 9, the inspection of the resist pattern 12 orientated in the Y direction can be carried out by the aforementioned method, whereas the inspection of the resist pattern 12 orientated in the X direction needs to be carried out from a plurality of directions since the emitted light is not reflected toward the direction of point A.

Used as the light source are lights 40, 42 and 44 for three light beams A, B and C, respectively, with different illumination angles. The positions of the respective lights can be changed along a predetermined are by a motor 46 which is controlled by a controller 48. The angles of the respective lights can be changed within a range of 15 to 75 degrees with reference to the top surface of the pattern on the work. Note that the number of lights is set to three for a further improvement of the detection sensitivity, but the detection can be feasible with at least one light or more. At least one of the lights is positioned to be perpendicular to the edge of the resist pattern on the wafer. In FIG. 7, the light A (40) is located at a position within a range of 48 to 52 degrees, the light C (44) is located at a position within a range of 16 to 18 degrees, and the light B (42) is located to be approximately coaxial with a CCD line sensor. The brightness of the light beams is adjusted by a power source 50 for lighting.

Similar to the lights, the position of a CCD line sensor camera 52 can be changed along the predetermined are by the motor 46 which is controlled by the controller 48. The light receiving angle of the camera 52 can be changed within a range of 15 to 75 degrees with reference to the top surface of the pattern on the work. A camera 54 for monitoring is attached to the camera 52. The outputs from the controllers 36 and 48 of the motor, the power source 50 for lighting and the cameras 50 and 52 are connected to an inspection personal computer (PC) 56. The inspection PC 56 controls each of the controllers and the power source for lighting, based on a predetermined automatic measuring program. By an instruction from the inspection PC 56, an image pickup optical system (positional relationship between the lights and line sensor camera) is arbitrarily set in accordance with an inspection target.

The image pickup optical system (positional relationship between the lights and the line sensor camera) and the angles shown in FIG. 7 are set as follows. Specifically, they are set so as to exclude unnecessary scattered light and diffracted light and to detect subtle shape changes of the resist with good sensitivity. Here, the most important point in designing the system is that the diffracted light from the inspected wafer does not return to an angle at which the line sensor camera 52 is placed, and only the reflected light from the resist edge portion is taken out with a good contrast. Accordingly, the diffracted light generated from the pattern on the wafer used as diffraction grating was calculated using a reflection grating model, and a positional relationship was set so that the diffracted light did not return to the angle at which the CCD line sensor exists when a dedicated reticle was used. It should be noted that an optimal pickup angle may be changed depending on the resist shape in setting the positional relationship.

Figure 10:
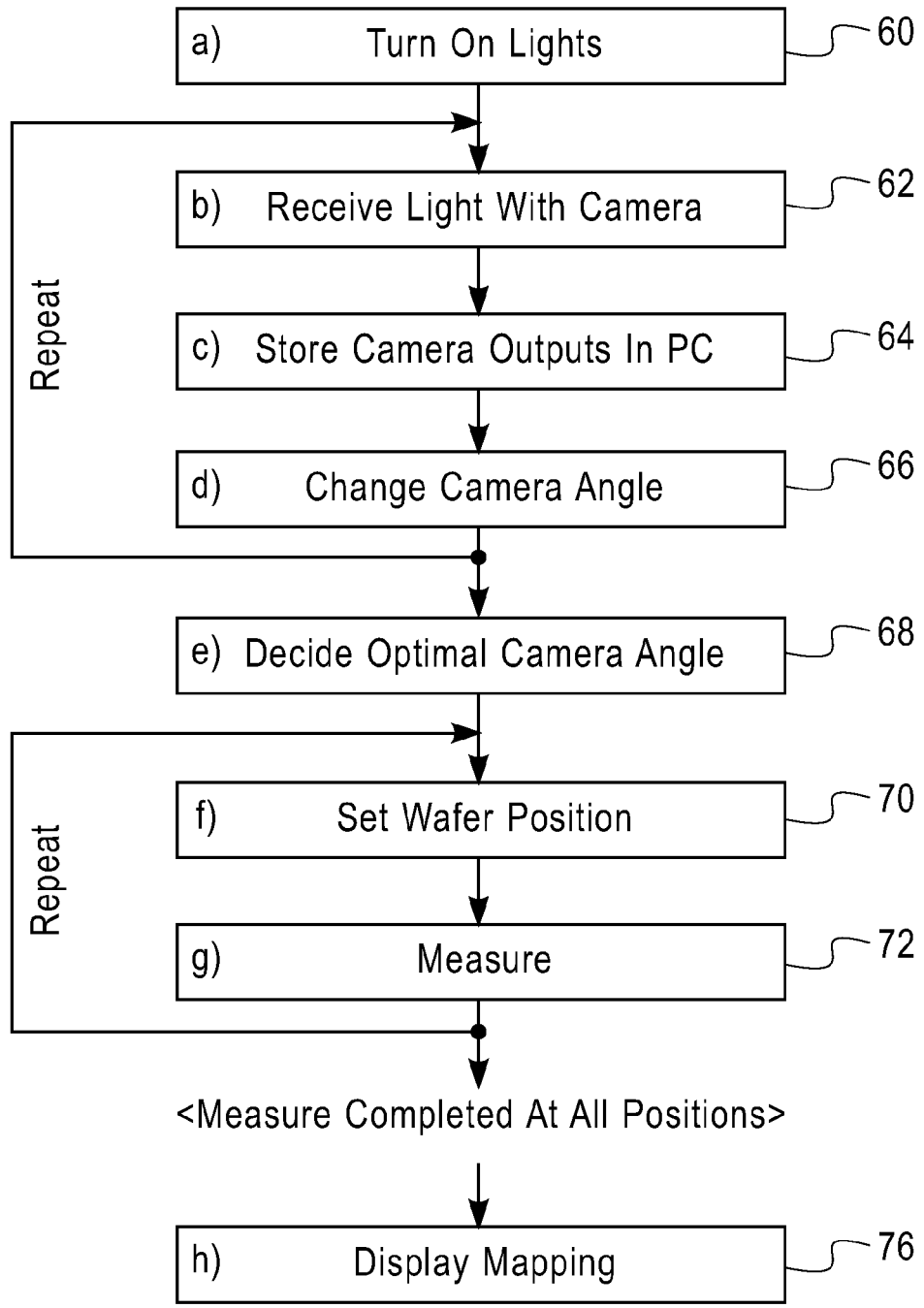
FIG. 10 is a view showing a control flow in an inspection PC of FIG. 7.

FIG. 10 shows a control flow (automatic measurement flow) by the use of the inspection PC 56 of FIG. 7. Three lights are turned on (step 60). The camera 52 receives the reflected light from the pattern on the wafer 32 (step 62). A capture card within the PC 56 receives the output from the camera 52 and the value (digital value) of the output is stored in a memory as image data (step 64). The size of the digital value corresponds to the amount of the reflected light. The angle of the camera is changed by controlling motor 46 (step 66). Steps 62 to 66 are repeated and the image data (digital value) captured at each angle is stored in the memory. Based on the digital values obtained, the PC 56 decides an angle of the camera 52 at which the detection sensitivity (density (intensity) of the image) is maximum (step 68). The camera 52 is fixed at the decided angle.

Measurement positions on the wafer are set by controlling the motor 34 (step 70). After the wafer is moved to the first measurement position, measurement is carried out similar to the steps 62 and 64, and image data is stored in the memory (step 72). The steps 70 and 72 are repeated, and the measurement is sequentially carried out while scanning the measurement positions on the wafer. At this time, since the camera 52 is a line sensor camera, the measurement is carried out while moving the wafer by each line at predetermined intervals. The measurement is conducted until all measurement points (lines) are completely measured. Using measurement data, the PC performs mapping of the image data at each position on the wafer as a two dimensional image (step 76). The presence or absence of the profile error (defocused portion) of the pattern on the wafer can be detected from the intensity (color density) in the mapped image information.

In the tests conducted by the inventors, almost none of the profile errors that are inevitably generated in a resist pattern could be measured with the conventional method utilizing diffraction. However, with the apparatus of the embodiment of the present invention in FIG. 7, the profile errors in a resist pattern can be detected as a clear image.

With the inspection apparatus of FIG. 7, exposure conditions for the photoresist can be adjusted based on the detected profile errors of the patterns. Therefore, the inspection apparatus can be incorporated into an exposure apparatus or stepper as a part of them. Specifically, there is an advantage that the exposure conditions (defocus) can be adjusted within a production line of semiconductor devices by providing the exposure apparatus or the stepper with means (flow) for adjusting the exposure conditions for the photoresist based on the profile errors of the patterns, which were detected by the inspection apparatus of FIG. 7. Further, it is possible to detect characteristics such as de-synchronization (error) between the wafer and the reticle possessed by the exposure apparatus or the stepper while being scanned, an autofocus tracking performance, an error of a leveling mechanism and distortion of a lens. Finally, description is given again regarding a case where the inspection apparatus of the present invention can be effectively used. As described earlier and shown in FIG. 3, in the inspection apparatus of the present invention, the profile error (defective formation) of the resist pattern 12 due to defocus is inspected by illuminating the edge of the resist pattern 12 with the illuminating light Li and receiving the reflected light Lr by the use of the CCD of the camera P. Therefore, the larger the ratio of the edge area of the resist pattern 12 is, the more the reflected light Lr can be received by the CCD of the camera P. Thus, the inspection apparatus 10 can be effectively used.

Figure 11:
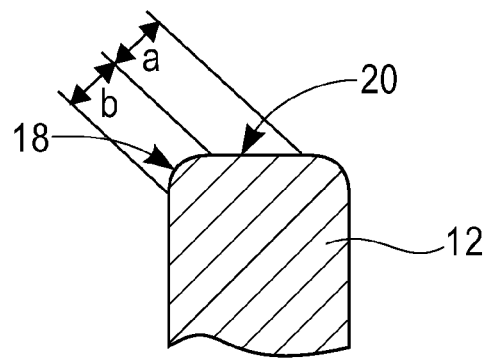
FIG. 11 is a view showing the illuminating light emitted onto a top surface of the resist pattern and the illuminating light emitted onto the edge.

As shown in FIG. 11, when a width of the illuminating light Li emitted to the top surface 20 of the resist pattern 12 is denoted by a and a width of the illuminating light Li emitted to the edge 18 is denoted by b, the ratio A of the illuminating light Li emitted to the edge 18 is expressed by the following equation.

$$A=b/(a+b)\%100$$

Figure 12:
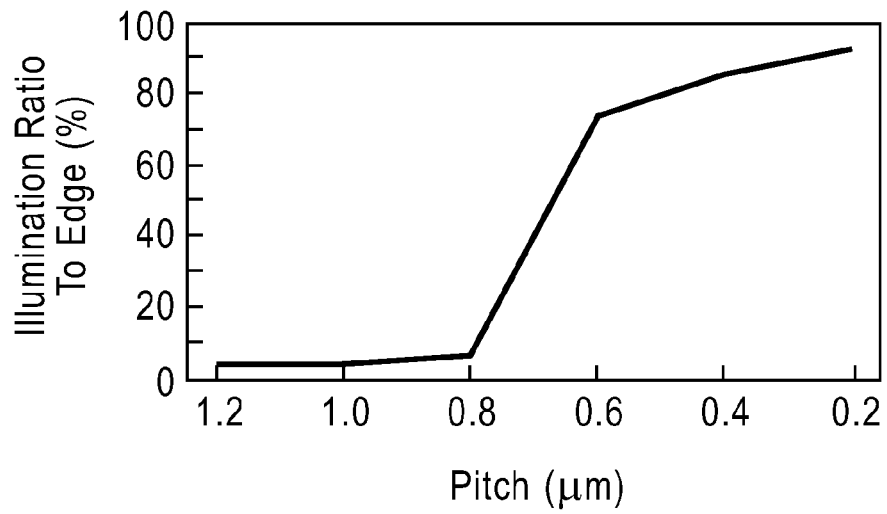
FIG. 12 is a graph showing the ratio of the illuminating light emitted to the edge thereof.
Figure 13:
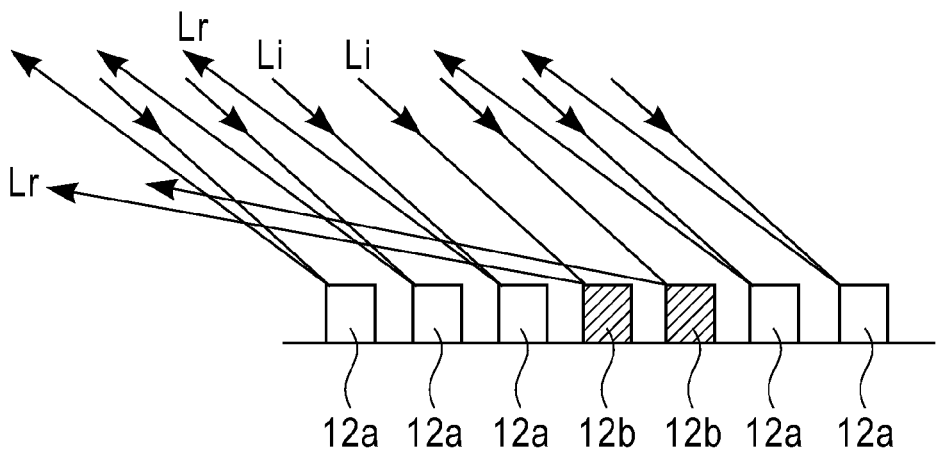
FIG. 13 is a view showing a difference in reflected light from the resist pattern of the defocused portion and the normal resist pattern.

FIG. 12 shows a graph of a relationship between the pitch of the resist pattern 12 (the sum of a pattern width and a pattern interval) and the ratio of the illuminating light Li emitted to the edge 18. As shown in FIG. 12, the ratio of the forgoing illuminating light Li is suddenly increased when the pitch is between 0.8 μm (pattern width/pattern interval=0.40 μm/0.40 μm) and 0.6 μm (pattern width/pattern interval=0.29 μm/0.31 μm). The inspection apparatus 10 of the present invention can be effectively used for the inspection of the resist pattern 12 having a pitch finer than 0.6 μm. However, according to the test conducted by the inventors, since the reflected light Lr can be confirmed, when the inspection is for the resist pattern 12 with a ratio of 50% or more of the illuminating light Li emitted to the edge 18, the inspection apparatus 10 can be used. This is because the ratio of the edge 18 in the entire resist pattern 12 is increased as the resist pattern 12 becomes finer, and the edge 18 is in a mirror-like state when the resist pattern 12 is viewed from the light source S. Therefore, if there is defective formation of the resist pattern 12 due to defocus, only the defectively formed portions (the resist patterns 12b shown by diagonally shaded portions in FIG. 13) have different angles of the reflected light Lr, and thereby the normal portion and the defocused portion can be distinguished. This is because there is difference in the amount of light received by the photodetector positioned at a predetermined angle.

The embodiment of the present invention has been described. However, the present invention is not limited to the above mentioned embodiment. For example, by enabling the positions of the light source S and the camera P to be changed within the aforementioned range, the reflected light Lr from the edge 18 of the resist pattern 12 can be received, and, in addition, diffracted light may be received by using the resist pattern 12 as diffraction grating depending on the positions of the light source S and the camera P. In this case, in order to receive the diffracted light, the mounting stage 16 is constructed to be able to slant at an arbitrary angle using a line passing though the center of the mounting stage 16 as an axis. By constructing as above, the inspection apparatus, unlike the foregoing inspection apparatus and the conventional inspection apparatus, can surely carry out the inspection even in the case where there is a plurality of pattern widths of the resist pattern 12.

Moreover, the defocused portion can be surely inspected by appropriately using the inspection apparatus 10 of the present invention and the conventional inspection apparatus utilizing diffracted light, depending on the ratio of the illuminating light Li emitted to the edge 18. When there is the plurality of pattern widths of the resist pattern 12, the inspection is surely carried out by using the inspection apparatus of the present invention and the conventional inspection apparatus.

Although LEDs are used for the light source S, the light source S may have a construction including a halogen lamp and filters instead of LEDs. Light including a wavelength between first and second wavelengths is taken out from the light of the halogen lamp by a filter which cuts off light with the first wavelength (short wavelength) or shorter and the filter which cuts off light with the second wavelength (long wavelength) or longer. The first and second wavelengths are those which conform to conditions of the aforementioned LEDs. A filter which passes only light including the wavelengths between the first and second wavelengths can be used instead of the two filters.

Apart from the above, the present invention can be carried out in a mode to which various improvements, alterations and modifications are added based on the knowledge of those skilled in the art, in the scope not departing from the gist of the present invention.

According to the present invention, a profile error (deviation) of a pattern having a cross section with projections and recesses can be detected easily with high accuracy. According to the present invention: presence or absence of a defocus which occurs during exposure of a resist pattern can be easily detected. According to the present invention, it is possible to easily detect the presence or absence of a profile error (deviation) of a fine resist pattern having a pattern width of about 0.1 micrometer or smaller, which could not be detected with a conventional method utilizing diffracted light.

The invention claimed is:

1. A pattern profile inspection apparatus for detecting a profile error of at least one pattern having a cross section with a projection and a recess, the inspection apparatus comprising:
   a plate on which the pattern is mounted;
   a light source which can change an angle of illuminating light to the pattern within a range of 15 to 75 degrees with reference to a top surface of the pattern; and
   a photodetector which can receive reflected light from the pattern at an angle within a range of 15 to 75 degrees with reference to the top surface of the pattern,
   wherein the profile error of the pattern is detected based on an amount of the reflected light which is received by the photodetector, from an edge between the top surface and a side surface of each of the patterns, wherein when the edge has a surface area of the pattern having the profile error, the amount of the reflected light received by the photodetector is greater than an amount of reflected light for the edge of the pattern not having the profile error.

2. A pattern profile inspection apparatus for detecting a profile error of a pattern having a cross section with a projection and a recess, the inspection apparatus comprising:
   a plate on which the pattern is mounted;
   a light source which can change an angle of illuminating light to the pattern within a range of 15 to 75 degrees with reference to a top surface of the pattern; and
   a photodetector which can receive reflected light from the pattern at an angle within a range of 15 to 75 degrees with reference to the top surface of the pattern,
   wherein an illumination angle from the light source is decided to be almost perpendicular to an edge between the top surface and a side surface of the pattern, wherein when the edge has a surface area of the pattern having the profile error, the amount of the reflected light received by the photodetector is greater than an amount of reflected light for the edge of the pattern not having the profile error.

3. The pattern profile inspection apparatus according to claim 2, further comprising at least one or more light sources having illumination angles different from said illumination angle.

4. The pattern profile inspection apparatus according to claim 2, wherein the light source includes a uniform surface emitting light source.

5. The pattern profile inspection apparatus according to claim 2, wherein the light source has an oblong shape such that the illuminating light has directivity.

6. The pattern profile inspection apparatus according to claim 2, wherein a light receiving angle of the photodetector is decided such that a ratio of the reflected light from the edge of the pattern out of said reflected light is maximum.

7. The pattern profile inspection apparatus according to claim 2, wherein the light receiving angle a (degree) of the photodetector is decided to meet a relationship expressed by an equation of $a=180-b-2c$, where b denotes the illumination angle (degree) with reference to the top surface of the pattern and c denotes an inclination angle (degree) of the edge with reference to a plane that is parallel to the top surface of the pattern.

8. The pattern profile inspection apparatus according to claim 2, wherein the photodetector includes a line sensor.

9. The pattern profile inspection apparatus according to claim 2, wherein the photodetector includes a CCD camera.

10. The pattern profile inspection apparatus according to claim 2, wherein the pattern includes a photoresist pattern provided on a substrate.

11. The pattern profile inspection apparatus according to claim 2, further comprising:
image processing means which receives an output signal of the photodetector and produces image information corresponding to an amount of the reflected light which is received by the photodetector;
drive means which changes positions of the light source and the photodetector in order to change the angle of the illuminating light and the light receiving angle of the reflected light; and
moving means which makes the plate move in order to change a position of the pattern illuminated with the illuminating light.

12. A pattern profile inspection apparatus for detecting defective formation of a thick pattern formed on a substrate, the inspection apparatus comprising:
a plate on which the pattern is mounted;
a light source which can change an angle of illuminating light to the pattern within a range of 15 to 75 degrees with reference to a top surface of the pattern; and
a photodetector which can receive reflected light from the pattern at an angle within a range of 15 to 75 degrees with reference to the top surface of the pattern,
wherein an illumination angle from the light source is decided such that a ratio of illuminating light emitted to an edge between the top surface and a side surface of the pattern out of the illuminating light is 50% or more,
wherein when the edge has a surface area of the pattern having the profile error, the amount of the reflected light received by the photodetector is greater than an amount of reflected light for the edge of the pattern not having the profile error.

13. An exposure apparatus which exposes a photoresist provided on a substrate, comprising a pattern profile inspection apparatus for detecting a profile error of at least one pattern of the photoresist having a cross section with a projection and a recess, the inspection apparatus including:
a plate on which the pattern is mounted;
a light source which can change an angle of illuminating light to the pattern within a range of 15 to 75 degrees with reference to a top surface of the pattern; and
a photodetector which can receive reflected light from the pattern at an angle within a range of 15 to 75 degrees with reference to the top surface of the pattern,
wherein a profile error of the pattern is detected based on an amount of the reflected light which is received by the photodetector and from an edge between the top surface and a side surface of the each of the patterns, wherein when the edge has a surface area of the pattern having the profile error, the amount of the reflected light received by the photodetector is greater than an amount of reflected light for the edge of the pattern not having the profile error.

14. A pattern profile inspection method which detects a profile error of at least one pattern having a cross section with a projection and a recess, the method comprising the steps of:
(a) illuminating a top surface of the pattern with light slanting with reference thereto;
(b) receiving reflected light which is reflected by an edge between the top surface and a side surface of the pattern;
(c) detecting the profile error of the pattern based on an amount of the received reflected light which is reflected by the edge; and
(d) mapping the profile error in the entire pattern as image information based on the detected profile error of each of the patterns.

15. The pattern profile inspection method according to claim 14, wherein the step of (a) illuminating the top surface of the pattern includes a step of emitting light to the edge almost perpendicularly.

* * * * *